(12) United States Patent
Evans et al.

(10) Patent No.: US 6,297,268 B1
(45) Date of Patent: Oct. 2, 2001

(54) IMIDAZOLES AS CHOLESTEROL LOWERING AGENTS

(75) Inventors: Ellen W. Evans, Sparta; Eileen A. Snyder, Kinnelon; Elmer J. Mirro, Sussex; Carol Merrill, Newton, all of NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 09/451,834

(22) Filed: Nov. 30, 1999

(51) Int. Cl.⁷ .................................................. A61K 31/415
(52) U.S. Cl. ............................................. 514/399; 514/396
(58) Field of Search .................................. 514/398, 399, 514/396, 397, 400

(56) References Cited

U.S. PATENT DOCUMENTS

| | | |
|---|---|---|
| 5,624,920 | 4/1997 | McKittrick et al. . |
| 5,631,365 | 5/1997 | Rosenblum et al. . |
| 5,633,246 | 5/1997 | McKittrick et al. . |
| 5,656,624 | 8/1997 | Vaccaro et al. . |
| 5,688,787 | 11/1997 | Burnett et al. . |
| 5,698,548 | 12/1997 | Dugar et al. . |
| 5,744,467 | 4/1998 | McKittrick et al. . |
| 5,767,115 | 6/1998 | Rosenblum et al. . |
| 5,990,147 * | 11/1999 | Aslanian ............................. 514/400 |

FOREIGN PATENT DOCUMENTS

| | | |
|---|---|---|
| 1364312 * | 1/1972 | (GB) . |

OTHER PUBLICATIONS

Mao, Monoclonal Antibodies to Human Plasma Low–Density Lipoproteins, *Clin. Chem.*, vol. 29, No. 11, 1983, pp. 1890–1897.

Miller, High Density Lipoproteins and Athersclerosis, *Ann.Rev. Med.*, vol. 31, 1980, pp. 97–108.

Brown, Lipoprotein Metabolism in the Macrophage, *Ann. Rev. Biochem.*, vol. 52, 1983, pp. 223–261.

* cited by examiner

Primary Examiner—Minna Moezie, J.D.
Assistant Examiner—Mojdeh Bahar
(74) Attorney, Agent, or Firm—Palaiyur S. Kalyanaraman

(57) ABSTRACT

In one embodiment, the present invention discloses a method and pharmaceutical composition for lowering serum cholesterol in a patient. The method comprises administering to the patient a pharmaceutical composition comprising a therapeutically effective cholesterol lowering amount of an imidazole. An example imidazole useful in the method and composition has the formula:

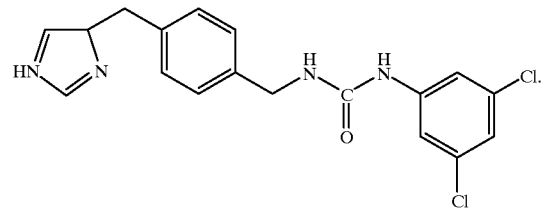

15 Claims, No Drawings

IMIDAZOLES AS CHOLESTEROL LOWERING AGENTS

FIELD OF THE INVENTION

The present invention generally relates to lowering of total serum cholesterol and to treating of diseases associated with high cholesterol in a patient in need thereof, by administering a therapeutically effective cholesterol lowering amounts of herein-disclosed imidazoles.

BACKGROUND OF THE INVENTION

Atherosclerotic coronary heart disease represents the major cause for death and cardiovascular morbidity in the western world. Despite recent declines in coronary heart disease ("CHD") mortality, CHD is still responsible for more than 500,000 deaths in the U.S. annually. It is estimated that CHD, directly or indirectly, causes the U.S. more than $100 billion a year. Risk factors for atherosclerotic coronary heart disease include, among several factors, hypertension, diabetes mellitus, family history, male gender, cigarette smoking and high serum cholesterol. A total cholesterol level in excess of 225–250 mg/dl is generally associated with a significant elevation of risk. Cholesteryl esters are a major component of atherosclerotic lesions and the major storage form of cholesterol in arterial wall cells. Lowering of plasma cholesterol in patients with hypercholesterolemia has been of intense focus in pharmaceutical research in recent years.

Typically, cholesterol is carried in the blood of warm-blooded animals in certain lipid-protein complexes such as, for example, chylomicrons, very low density lipoprotein ("VLDL"), low density lipoprotein ("LDL"), and high density lipoprotein ("HDL"). It is widely accepted that LDL functions in a way that directly results in deposition of the LDL cholesterol in the blood-vessel wall and that HDL functions in a way that results in the HDL picking up cholesterol from the vessel wall and transporting it to the liver where it is metabolized [M. S. Brown and J. L. Goldstein, *Ann. Rev. Biochem.*, 52 (1983), 223; G. L. Miller, *Ann. Rev. Med.*, 31 (1980), 97]. For example, in various epidemiological studies, the LDL cholesterol levels correlate well with the risk of coronary heart disease whereas the HDL cholesterol levels are inversely associated with coronary heart disease [J. G. Patton et al, *Clin. Chem.*, 29 (1983), 1890]. It is generally accepted by those skilled in the art that reduction of abnormally high LDL cholesterol levels is effective therapy not only in the treatment of hypercholesterolemia but also in the treatment of atherosclerosis. Accordingly, it is desirable to provide a method for reducing LDL cholesterol in patients with hypercholesterolemia.

Several products are commercially available from drug manufacturers for the lowering of cholesterol. Some illustrative types and commercial products are: resins (for example, QUESTRAN® which is cholestyramine ion exchange resin from Bristol-Myers Squibb Corporation, Princeton, N.J.; and COLESTID® which is the hydrochloride of the polymer of N-(2-aminoethyl)-N'-[2-[(2-aminoethyl)amino]ethyl]-1,2-ethanediamine with (chloromethyl)oxirane) available from Pharmacia-Upjohn Company, Peapack, N.J.); fibrates (for example, LOPID® which is 5-(2,5-dimethylphenoxy)-2,2-dimethylpentanoic acid available from Warner-Lambert Company, Morris Plains, N.J.; and TRICOR® which is a fenofibrate available from Abbott Laboratories, Chicago, Ill.); and statins (for example, lovastatin as MEVACOR® available from Merck & Company, Whitehouse Station, N.J.; fluvastatin as LESCOL® from Novartis Corporation, East Hanover, N.J.; simvastatin as ZOCOR® from Merck & Company; pravastatin as PRAVACHOL® from Bristol Myers Squibb Corporation; atorvastatin as LIPITOR® from Warner-Lambert Company; and cerivastatin as BAYCOL® from Bayer Corporation, West Haven, Conn.).

U.S. Pat. Nos. 5,767,115; 5,744,467; 5,698,548; 5,688,787; 5,656,624; 5,633,246; 5,631,365; and 5,624,920 (all assigned to Schering Corporation, Kenilworth, N.J.) disclose various azetidinones and substituted p-lactam compounds as cholesterol lowering agents.

There is a continuing interest in finding novel cholesterol lowering agents.

It is an objective of this invention to find useful cholesterol lowering agents.

It is a farther objective of this invention to find methods of lowering cholesterol and treating diseases associated with high cholesterol, using novel compounds.

Other objectives and advantages of the present invention will be apparent to those skilled in the art from the accompanying description and claims.

SUMMARY AND DESCRIPTION OF THE INVENTION

This invention arises from a series of studies on the utility of imidazoles in lowering of serum cholesterol. It has now been found that certain imidazole compounds surprisingly exhibit desirable and therapeutically effective cholesterol lowering properties. Thus, one embodiment of the present invention comprises the use of therapeutically effective amounts of an imidazole compound (or an enantiomer, stereoisomer, tautomer, pharmaceutically acceptable salt or derivative of said imidazole) in the lowering of serum cholesterol, as well as in the treatment of hyperlipidemia or hypercholesterolemia, atherosclerosis, and other cardiovascular diseases associated with high cholesterol. Imidazole compositions are provided herein for use alone by themselves, as well as in combination with other suitable agents, said agents including, but not limited to, statins, resins, fibrates, azetidinones and the like, for the lowering of serum cholesterol as well as for the treatment of the above-mentioned diseases as well as other related diseases.

In another embodiment, the invention discloses a method to lower total serum cholesterol and lower LDL cholesterol in a patient in need thereof. The method comprises administering to said patient a composition comprising a therapeutically effective cholesterol lowering amount of a suitable imidazole or an enantiomer, stereoisomer, tautomer, pharmaceutically acceptable salt or derivative of said imidazole.

Yet another embodiment of the present invention discloses a method to inhibit the progression of atherosclerosis in a patient in need thereof, by administering to said patient a pharmaceutical composition comprising a therapeutically effective antiatherosclerotic amount of a suitable imidazole or an enantiomer, stereoisomer, tautomer, pharmaceutically acceptable salt or derivative of said imidazole.

Still another embodiment of the present invention discloses a general method of treating cardiovascular diseases in a patient in need of such treatment by administering to said patient a pharmaceutical composition comprising a therapeutically effective amount of a suitable imidazole (or an enantiomer, stereoisomer, tautomer, pharmaceutically acceptable salt or derivative of said imidazole) and a pharmaceutically acceptable carrier.

As used herein, the term "patient" refers to warm-blooded animals or mammals, including humans, who are in need of the specified treatment.

The term "hypercholesterolemia" refers to a disease state characterized by levels of total serum cholesterol or of LDL cholesterol which are elevated by a clinically significant amount over that considered normal by those of ordinary skill in the art. The identification of those patients who are in need of treatment for hypercholesterolemia is well within the knowledge and ability of one skilled in the art. For example, individuals who have serum cholesterol levels or LDL cholesterol levels, as determined by clinical laboratory tests, which are substantially and chronically elevated over that considered normal by those of ordinary skill in the art, are patients in need of treatment for hypercholesterolemia. A clinician skilled in the art can readily identify, by the use of clinical tests, physical examination and medical/family history, those patients who are suffering from hypercholesterolemia and those who are at risk of developing hypercholesterolemia and thus readily determine if an individual is a patient in need of treatment for hypercholesterolemia.

A therapeutically effective cholesterol lowering amount or amounts of a suitable imidazole refers to an amount of the imidazole, which is effective in reducing serum cholesterol levels or LDL cholesterol levels in a patient in need thereof. As such, successful treatment of a patient for hypercholesterolemia is understood to include reducing a patient's serum cholesterol or LDL cholesterol levels. Successful treatment for hypercholesterolemia is also understood to include prophylaxis in preventing clinically significant elevations in serum cholesterol or in LDL cholesterol levels in a patient who is at risk of the development of hypercholesterolemia.

The term "atherosclerosis" refers to a disease state characterized by the development and growth of atherosclerotic lesions or plaque. The identification of those patients who are in need of treatment for atherosclerosis is well within the knowledge and ability of one skilled in the art. For example, individuals who are either suffering from clinically significant atherosclerosis or who are at risk of developing atherosclerosis are patients in need of treatment for atherosclerosis. A clinician skilled in the art can readily determine, by the use of clinical tests, physical examination and medical/family history, if an individual is a patient in need of treatment for atherosclerosis.

A therapeutically effective antiatheroslerotic amount of a suitable imidazole refers to an amount, which is effective in inhibiting the development or growth of ateroclerosis in a patient in need thereof. Therefore, successful treatment of a patient for atherosclerosis is understood to include effectively slowing, interrupting, arresting, or stopping atherosclerotic lesion or plaque development or growth and does not necessarily indicate a total elimination of the atherosclerosis. It will be further understood and appreciated by those skilled in the art that successful treatment for atherosclerosis can include prophylaxis in preventing atherosclerotic lesion or plaque formation.

The imidazoles useful in the embodiments of the invention have the general structure shown in Formula I:

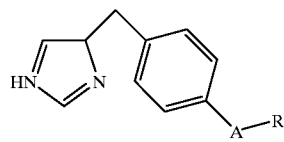

Formula I wherein

A is —CH$_2$—NH—CO—NH—; —CH$_2$—O—CO—NH— or —CH$_2$—CH$_2$—CO —NH—(CH$_2$)$_m$—;

m is 0, 1 or 2; and

R is the moiety:

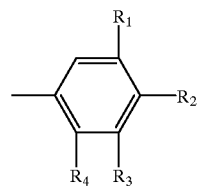

wherein at least two of R$_1$, R$_2$, R$_3$ and R$_4$ are hydrogen and the rest are independently selected from H, halogen (e.g., Br, I, F, or Cl), CH$_3$, CF$_3$, OCH$_3$, OCF$_3$ and CN; with the proviso that when A is —CH$_2$—O—CO—NH— and R$_1$, R$_3$ and R$_4$ are all hydrogen, then R$_2$ cannot be Cl. The general Formula I also includes the enantiomers, stereoisomers, tautomers, pharmaceutically acceptable salts or derivatives of the imidazole of Formula I.

Such imidazoles of Formula I are disclosed as H$_3$ receptor antagonists in pending U.S. patent application Ser. No. 09/186,492, filed Nov. 5, 1998 now U.S. Pat. No. 5,990,147. The superior cholesterol-lowering and antiatheroslerotic properties of such imidazoles, however, are surprising and have not been reported before.

This invention preferably includes the use of compounds of Formula I wherein at least two of R$_1$, R$_2$, R$_3$ and R$_4$ are hydrogen and the rest are independently selected from H, F, Cl, CH$_3$, CF$_3$, OCH$_3$, OCF$_3$ and CN, for the lowering of serum cholesterol and treating of related diseases stated above.

This invention also includes use of compounds of Formula I wherein at least two of R$_1$, R$_2$, R$_3$ and R$_4$ are hydrogen and the rest are Cl, for the lowering of serum cholesterol and treating of related diseases stated above.

This invention further includes use of compounds of Formula I wherein at least two of R$_1$, R$_2$, R$_3$ and R$_4$ are hydrogen and the rest are Cl, and A is —CH$_2$—NH—CO—NH—, for the lowering of serum cholesterol and treating of related diseases stated above.

Illustrative imidazole compounds useful in the practice of this invention include:

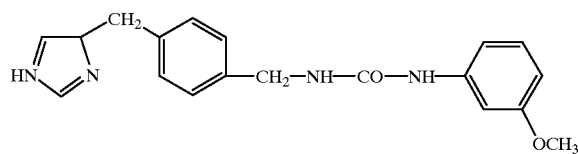

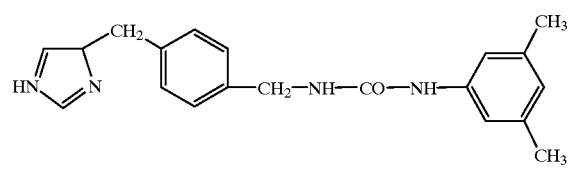
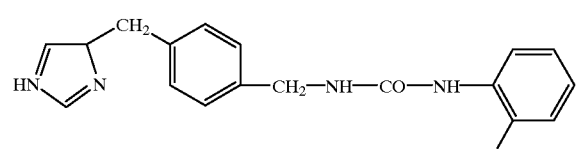
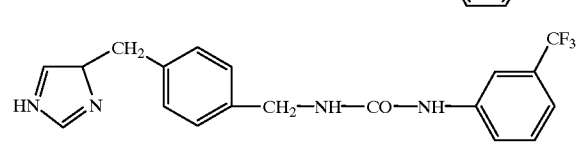
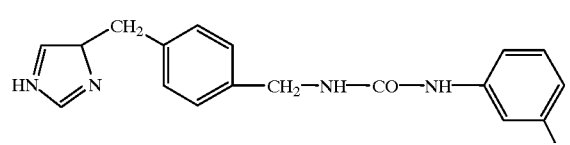
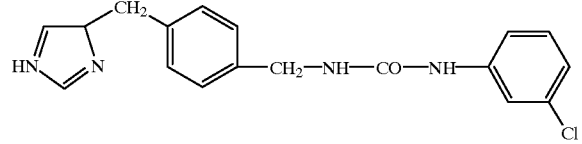
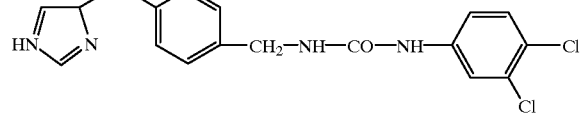
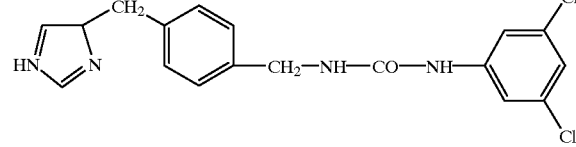
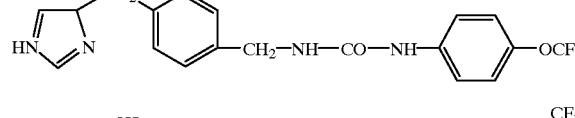
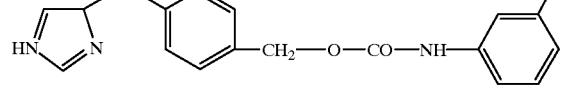
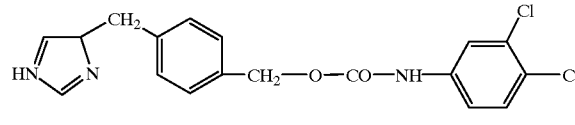
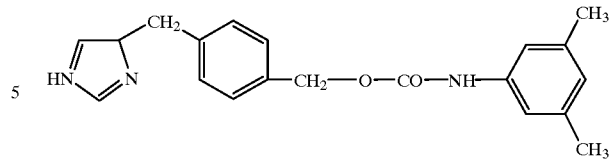
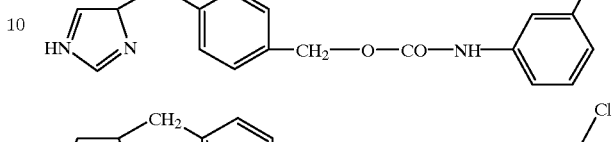
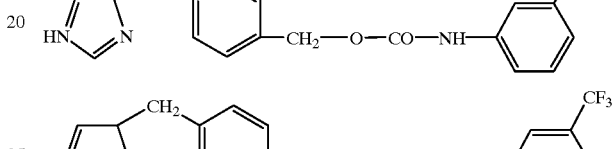
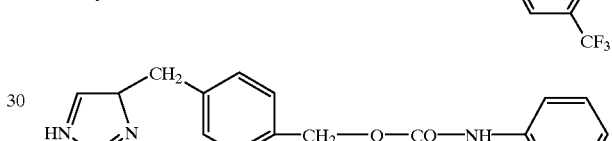
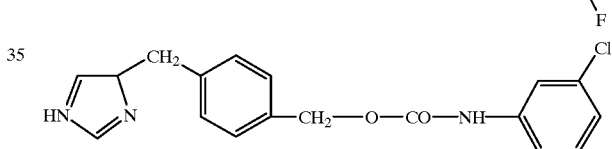
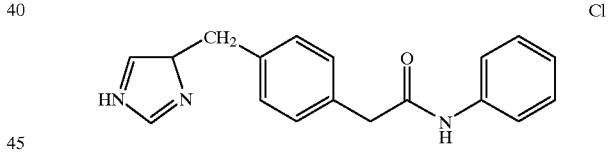
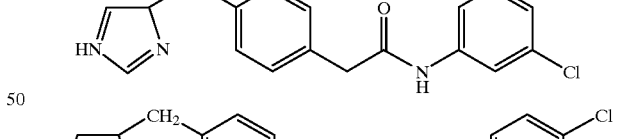
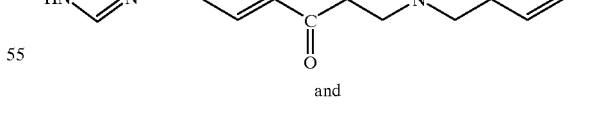
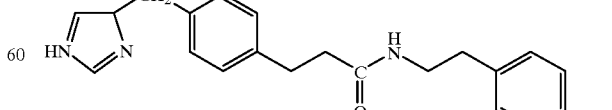
and
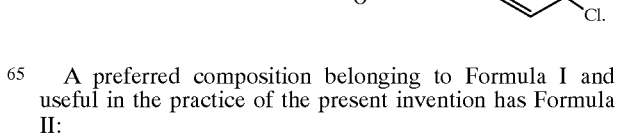
A preferred composition belonging to Formula I and useful in the practice of the present invention has Formula II:

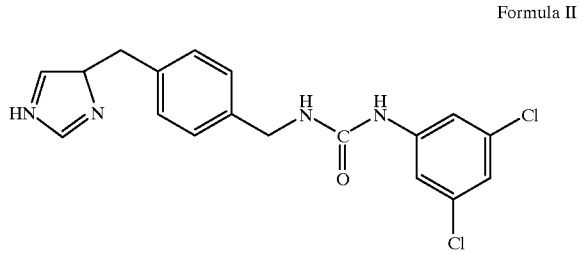

Formula II as well as the enantiomers, stereoisomers, tautomers, pharmaceutically acceptable salts or derivatives of the compound of Formula II.

The compound of Formula II is also disclosed in the above-identified pending patent application, Ser. No. 09/186,492 now U.S. Pat. No. 5,990,147. The imidazole of Formula II was surprisingly found to have efficacious cholesterol-lowering activity which is further discussed more in the EXAMPLES section below.

In another embodiment, this invention provides pharmaceutical compositions comprising the imidazole of Formula I as an active ingredient. The pharmaceutical compositions generally additionally comprise a pharmaceutically acceptable carrier diluent, excipient or carrier (collectively referred to as carrier materials herein). Because of their cholesterol-lowering activity, such pharmaceutical compositions possess utility in treating hypercholesterolemia, atherosclerosis and like diseases.

In yet another embodiment, the present invention discloses methods for preparing pharmaceutical compositions to treat atheroclerosis and hypercholesterolemia, said compositions comprising the imidazole of Formula I as an active ingredient.

A therapeutically effective cholesterol lowering or anti-atherosclerotic dose can be readily determined by the use of conventional techniques and by observing results obtained under analogous circumstances. In determining the effective dose, a number of factors are considered including, but not limited to: the species of the patient, its size, age, gender and general health, the specific disease involved, the degree of or involvement or severity of the disease, the response of the individual patient, the particular imidazole in the composition administered, type of any co-compound(s) in the composition administered, the bioavailability of the preparations administered, the dose regimen selected, and the use of any concomitant medication. Such techniques are well known to those skilled in the art.

A therapeutically effective cholesterol lowering or anti-atherosclerotic amount of the imidazole useful in the practice of the invention will generally vary from about 1 mg per kilogram of body weight of the patient per day (mg/kg/day) to about 5 grams per kilogram of body weight per day (gm/kg/day). A daily dose of from about 1 mg/kg to about 500 mg/kg is preferred. Generally, the human oral dosage form containing the active ingredients can be administered 1 or 2 times per day. The amount and frequency of the administration will be regulated according to the judgment of the attending clinician.

In the pharmaceutical compositions and methods of the present invention, the active ingredients may be administered in any form or mode which makes the compound bioavailable in effective amounts, including oral and parenteral routes. Some such modes and routes may be, for example, oral, subcutaneous, intramuscular, intravenous, transdermal. intranasal, rectal, and the like. Oral administration is generally preferred. Some suitable oral forms are, for example, oral tablets, capsules (either solid-filled, semi-solid filled or liquid filled), powders for constitution, oral gels, elixirs, dispersible granules, syrups, suspensions, and the like, and consistent with conventional pharmaceutical practices. One skilled in the art of preparing pharmaceutical formulations can readily select the proper form, mode and method of administration depending upon, for example, the disease state to be treated, the stage of the disease, and other relevant circumstances.

A compound of Formula I can be administered in the pharmaceutical compositions or medicaments which may be made by combining a compound of Formula I with a oral non-toxic edible pharmaceutically acceptable inert carrier or excipient, the proportion and nature of which are determined by the chosen route of administration, and standard pharmaceutical practice. The carrier or excipient may be a solid, semi-solid, or liquid material which is suitable to serve as a vehicle or medium for the active ingredient. They may be enclosed in gelatin capsules or compressed into tablets. Examples of suitable carriers are lactose, starch, sucrose, cellulose, magnesium stearate, dicalcium phosphate, calcium sulfate, talc, mannitol, ethyl alcohol (liquid forms) and the like, as well as mixtures thereof.

Oral therapeutic administration may be in the form of tablets, troches, capsules, elixirs, suspensions, syrups, wafers, chewing gums and the like. These preparations should contain at least 4% of a compound of Formula I, the active ingredient, but may be varied depending upon the particular form and may conveniently be between 4–96% of the weight of the unit. The amount of the active ingredient present in compositions is such that a unit dosage form suitable for administration will be obtained.

Moreover, when desired or needed, suitable binders, lubricants, disintegrating agents ("disintegrants"), and coloring agents may also be incorporated in the composition. Binders, lubricants and disintegrants are discussed later. Sweetening agents such as, for example, sucrose, saccharin and the like, and flavoring agents such as, for example, peppermint, methyl salicylate, orange flavoring and the like, and suitable preservatives, dyes, colorings and flavors may also be included in the pharmaceutical composition where appropriate. When the dosage form is a capsule, it may additionally contain a liquid carrier such as polyethylene glycol or a fatty oil. Other dosage unit forms may contain other various materials which modify the physical form of the dosage unit, for example, as coatings. Thus, tablets or pills may be coated with sugar shellac or other enteric coating agents. Some of the terms noted above, namely disintegrants, diluents, lubricants, binders and the like, are discussed in more detail below.

For the purpose of parenteral administration, a compound of Formula I may be incorporated into a solution or suspension. These preparations should contain at least 0.1% of the active imidazole ingredient of the invention, but may be varied between 0.1 and about 50% of the weight thereof. The amount of the active ingredient present in such compositions is such that a suitable dosage will be obtained. Parenteral preparations may be enclosed in ampules, disposable syringes, or multiple dose vials made of glass or plastic.

Additionally, the above-noted pharmaceutical compositions may be formulated in sustained release form to provide the rate controlled release of any one or more of the components or active ingredients to optimize the desired therapeutic effects, i.e. the cholesterol lowering activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

Liquid form preparations include solutions, suspensions and emulsions. As an example may be mentioned water or water-propylene glycol solutions for parenteral injections or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier such as inert compressed gas, e.g. nitrogen.

For preparing suppositories, a low melting wax such as a mixture of fatty acid glycerides, for example cocoa butter, is first melted, and the active ingredient is dispersed homogeneously therein by stirring or similar mixing. The molten homogeneous mixture is then poured into convenient sized molds, allowed to cool and thereby solidify.

Also included are solid form preparations which are intended to be converted, shortly before use, to liquid form preparations for either oral or parenteral administration. Such liquid forms include solutions, suspensions and emulsions.

The solutions or suspensions stated earlier may also include one or more of the following adjuvants depending on the solubility and other properties of a compound of Formula I: sterile diluents such as water for injection, saline solutions, fixed oils, polyethylene glycols, glycerin, propylene glycol or other suitable synthetic solvents; antimicrobial agents such as benzyl alcohol or methyl paraben; antioxidants such as ascorbic acid or sodium bisulfite; chelating agents such as ethylene diamine tetraacetic acid or its salts; buffers such as acetates, citrates or phosphates; and agents for the adjustment of toxicity such as sodium chloride or dextrose.

The pharmaceutical compositions may also be deliverable transdermally. The transdermal compositions may take the form of creams, lotions, aerosols and/or emulsions and can be included in a transdermal patch of the matrix or reservoir type as are conventional in the art for this purpose.

A stated earlier, preferably the compound is administered orally. Preferably the pharmaceutical preparation is in a unit dosage form. In such form, the preparation is subdivided into suitably sized unit doses containing appropriate quantities of the active components, e.g., an effective amount of the active imidazole ingredient, to achieve the desired purpose.

Capsule—refers to a special container or enclosure made of methyl cellulose, polyvinyl alcohols, or denatured gelatins or starch for holding or containing compositions comprising the active ingredients. Hard shell capsules are typically made of blends of relatively high gel strength bone and pork skin gelatins. The capsule itself may contain small amounts of dyes, opaquing agents, plasticizers and preservatives.

Tablet—refers to a compressed or molded solid dosage form containing the active ingredients with suitable diluents. The tablet can be prepared by compression of mixtures or granulations obtained by wet granulation, dry granulation or by compaction.

Oral gels—refers to the active ingredients dispersed or solubilized in a hydrophillic semi-solid matrix.

Powders for constitution refers to powder blends containing the active ingredients and suitable diluents which can be suspended in water or juices.

Diluent—refers to substances that usually make up the major portion of the composition or dosage form. Suitable diluents include sugars such as lactose, sucrose, mannitol and sorbitol; starches derived from wheat, corn, rice and potato; and celluloses such as microcrystalline cellulose. The amount of diluent in the composition can range from about 10 to about 90% by weight of the total composition, preferably from about 25 to about 75%, more preferably from about 30 to about 60% by weight, even more preferably from about 12 to about 60%.

Disintegrants—refers to materials added to the composition to help it break apart (disintegrate) and release the medicaments. Suitable disintegrants include starches; "cold water soluble" modified starches such as sodium carboxymethyl starch; natural and synthetic gums such as locust bean, karaya, guar, tragacanth and agar; cellulose derivatives such as methylcellulose and sodium carboxymethylcellulose; microcrystalline celluloses and cross-linked microcrystalline celluloses such as sodium croscarmellose; alginates such as alginic acid and sodium alginate; clays such as bentonites; Primogel; and effervescent mixtures. The amount of disintegrant in the composition can range from about 2 to about 15% by weight of the composition, more preferably from about 4 to about 10% by weight.

Binders—refers to substances that bind or "glue" powders together and make them cohesive by forming granules, thus serving as the "adhesive" in the formulation. Binders add cohesive strength already available in the diluent or bulking agent. Suitable binders include sugars such as sucrose; starches derived from wheat, corn, rice and potato; natural gums such as acacia, gelatin and tragacanth; derivatives of seaweed such as alginic acid, sodium alginate and ammonium calcium alginate; polyethyleneglycol; waxes; cellulosic materials such as methylcellulose and sodium carboxymethylcellulose and hydroxypropylmethylcellulose; polyvinylpyrrolidone; and inorganics such as magnesium aluminum silicate. The amount of binder in the composition can range from about 2 to about 20% by weight of the composition, more preferably from about 3 to about 10% by weight, even more preferably from about 3 to about 6% by weight.

Lubricant—refers to a substance added to the dosage form to enable the tablet, granules, etc. after it has been compressed, to release from the mold or die by reducing friction or wear. Suitable lubricants include metallic stearates such as magnesium stearate, calcium stearate or potassium stearate; stearic acid; high melting point waxes; and water soluble lubricants such as sodium chloride, sodium benzoate, sodium acetate, sodium oleate, polyethylene glycols and d'1-leucine. Lubricants are usually added at the very last step before compression, since they must be present on the surfaces of the granules and in between them and the parts of the tablet press. The amount of lubricant in the composition can range from about 0.2 to about 5% by weight of the composition, preferably from about 0.5 to about 2%, more preferably from about 0.3 to about 1.5% by weight.

Glidents—materials that prevent caking and improve the flow characteristics of granulations, so that flow is smooth and uniform. Suitable glidents include silicon dioxide and talc. The amount of glident in the composition can range from about 0.1% to about 5% by weight of the total composition, preferably from about 0.5 to about 2% by weight.

Coloring agents—excipients that provide coloration to the composition or the dosage form. Such excipients can include food grade dyes and food grade dyes adsorbed onto a suitable adsorbent such as clay or aluminum oxide. The amount of the coloring agent can vary from about 0.1 to about 5% by weight of the composition, preferably from about 0.1 to about 1%.

Bioavailability—refers to the rate and extent to which the active drug ingredient or therapeutic moiety is absorbed into the systemic circulation from an administered dosage form as compared to a standard or control.

Conventional methods for preparing tablets are known. Such methods include dry methods such as direct compression and compression of granulation produced by compaction, or wet methods or other special procedures. Conventional methods for making other forms for administration such as, for example, capsules, suppositories and the like, are also well known.

In another embodiment of the present invention, the active ingredient in the pharmaceutical compositions and methods of the present invention may be a mixture comprising the imidazole compositions of Formula I and a material such as, for example, statin, resin, fibrate, azetidinone and the like, the mixture being useful for the lowering of serum cholesterol as well as for the treatment of the above-mentioned diseases and other related diseases. Illustrations of suitable statins, resins, and fibrates are disclosed earlier in the "Background of the Invention" section. U.S. patents disclosing azetidinones useful in the present invention are those that are disclosed in the "Background of the Invention". An example such azetidinone disclosed in U.S. Pat. No. 5,767,115 has Formula III:

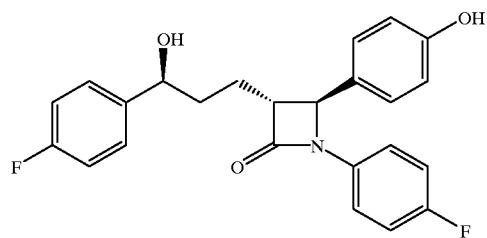

Formula III

Particularly preferred such additional active ingredient is a statin or an azetidinone. Thus, for example, the active ingredient useful in the present invention may contain a combination of the imidazole composition of Formula I and a statin (or an azetidinone of Formula III) in a weight ratio 5:95 to 95:5 respectively, mixed together in a suitable form discussed above and delivered in a suitable form and method also discussed above. Thus, for example, in a solid form, a compound of Formula II and atorvastatin (or the azetidinone of Formula III) may be combined in a 50:50 weight ratio as active ingredients, additional suitable ingredients such as, for example, carriers, disintegrants, binders and the like may be added and the entire mixture compressed into a tablet form in desired dosage amounts. Such a composition and method can take advantage cholesterol lowering properties of both the compound of Formula II and atorvastatin (or the azetidinone of Formula III).

The following EXAMPLES are being provided to further illustrate the present invention. These Examples demonstrate the cholesterol lowering ability of the compound of Formula II in rats and monkeys. They are for illustrative purposes only; the scope of the invention is not to be considered limited in any way thereby. It will be apparent to those skilled in the art that many modifications, variations and alterations to the present disclosure, both to materials and methods, may be practiced. Such modifications, variations and alterations are also intended to be within the spirit and scope of the present invention.

EXAMPLES

Example 1
Preparation of a Compound of Formula II

Compound of Formula II was prepared as disclosed in pending patent application, Ser. No. 09/186,492, filed Sep. 5, 1998 now U.S. Pat. No. 5,990,147.

Example 2
Evaluation of the Cholesterol Lowering Properties of the Compound of Formula II in Rats A homogeneous suspension of the compound of Formula II in aqueous methyl cellulose (aqueous methyl cellulose concentration: 0.4 percent weight/volume) was prepared for these studies and stored at ambient temperature conditions. The amount of the suspension fed to each rat was calculated to provide the desired dosage of the compound of Formula II (see below) for that rat.

Six-week-old rats (Rat/Crl:CD®(SD)BR VAF/Plus®, supplied by Charles River Laboratories, Kingston, N.Y.; ten rats per sex per group) were given single daily oral doses (via gavage tube) of the compound of Formula II (30, 100 or 300 mg/kg of body weight of the rat) as the above-stated suspension for 15 to 16 days. Twenty-seven additional rats were similarly dosed and bled for plasma analysis after one and 14 doses and served to confirm absorption of the compound of Formula II in rats. The rats were housed individually in suspended stainless steel wire mesh cages and were fed with a meal of Certified Rodent Diet® 5002 available from PMI® Feeds, Incorporated, St. Louis, Mo. Tap water was provided ad libitum during the study period. Blood was collected at necropsy over two days (after 15–16 doses), and serum chemistry parameters were measured.

Lower serum cholesterol concentrations, compared with concurrent control data, occurred in a dose-dependent fashion in low-dose male rats and in mid- and high-dose male and female rats. Serum triglyceride concentrations were found to be lower in mid- and high-dose male rats and female rshan in concurrent control rats. The results obtained at necropsy (after 15–16 doses) are given in Table 1 for both the male and female rats:

TABLE 1

Group Mean Serum Cholesterol and Triglyceride Concentrations in Rats Given the compound of Formula II in 0.4% (w/v) aqueous methylcellulose

| | Males | | | | Females | | | |
|---|---|---|---|---|---|---|---|---|
| | 0 mg/kg | 30 mg/kg | 100 mg/kg | 300 mg/kg | 0 mg/kg | 30 mg/kg | 100 mg/kg | 300 mg/kg |
| Cholesterol (mg/dl) | 34.7 | 20.9 | 16.9 | 12.3 | 29.7 | 26.5 | 19.4 | 16.0 |
| Triglycerides (mg/dl) | 40.7 | 37.2 | 27.8 | 21.2 | 22.4 | 20.5 | 13.6* | 16.3* |

*Group mean excludes individuals with values <10 mg/kg; actual mean would be lower The results demonstrate that the compound of Formula II caused dose-dependent lower serum cholesterol in male rats at doses of 30, 100, or 300 mg/kg of body weight. Lower serum cholesterol concentrations were also seen in female rats administered 100 or 300 mg/kg of body weight, compared with concurrent control rats. Lower serum triglyceride concentrations occurred in both male and female rats administered 100 or 300 mg/kg of body weight the compound of Formula II.

Example 3

Evaluation of the Cholesterol Lowering Properties of the compound of Formula II in monkeys Similar to Example 2, a homogeneous suspension of the compound of Formula II in aqueous methyl cellulose (0.4 percent weight/volume) was prepared for these studies and stored at ambient temperature conditions. The amount of the suspension fed to each monkey was calculated to provide the desired dosage of the compound of Formula II (given below) for that monkey.

Adult cynomolgus monkeys (four per sex per group, *Macaca fascicularis* monkey, supplied by Charles River BRF Incorporated, Houston, Tex.) were given single daily oral doses (gavage) of the compound of Formula II (30, 100 or 300 mg/kg of body weight) in the form of the above-stated suspension for 16 to 18 days. Plasma levels and pharmacokinetics of the compound of Formula II in these monkeys were determined after one and 16 doses and served to confirm absorption of the compound of Formula II in the monkeys. The monkeys were fed with nutritionally adequate amounts of PMI Inc. Certified Primate Diet® #46 (available from PMI Feeds, Incorporated) daily, at least one hour after dosing was completed. Certified monkey treats were offered daily. Tap water was provided ad libitum. Blood was collected and serum chemistry parameters were measured twice pretest and after 14 daily doses (22 hours after the $14^{th}$ dose).

Mild to moderate decreases in serum cholesterol, compared with pretest and concurrent and/or historical control data, occurred in all dosed monkeys. The decreases were generally dose-dependent, except that there was no real difference between mid- and high-dose females. The values for Group Mean Cholesterol for the monkeys after 14 doses are given in Table 2 below:

TABLE 2

% Decrease in Group Mean Cholesterol from Last Pretest to after-14-doses in monkeys Given the compound of Formula II in 0.4% (w/v) aqueous methylcellulose

|  | 0 mg/kg | 30 mg/kg | 100 mg/kg | 300 mg/kg |
| --- | --- | --- | --- | --- |
| Male | +02 | −25 | −46 | −61 |
| Female | −03 | −24 | −63* | −59 |

* n= 3; excludes No. 22F, which was sacrificed on Day 9

These results demonstrated that the compound of Formula II caused mildly to moderately decreased cholesterol in all monkeys dosed with 30, 100, or 300 mg/kg, in a generally dose-dependent fashion.

What is claimed is:

1. A method of lowering serum cholesterol in a patient suffering from hypercholesterolemia, the method comprising administering to said patient a composition comprising a therapeutically effective cholesterol lowering amount of an imidazole, or an enantiomer, stereoisomer, tautomers, pharmaceutically acceptable salt, or solvate thereof, wherein said imidazole is selected from the following compounds:

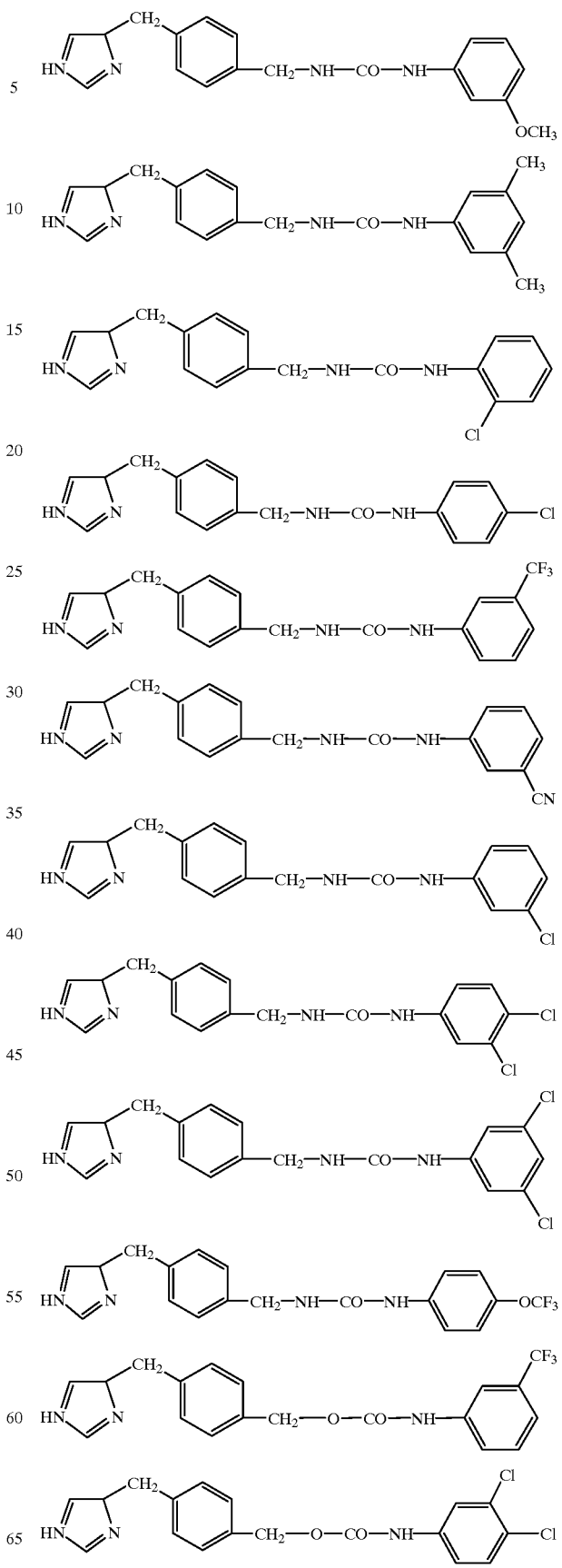

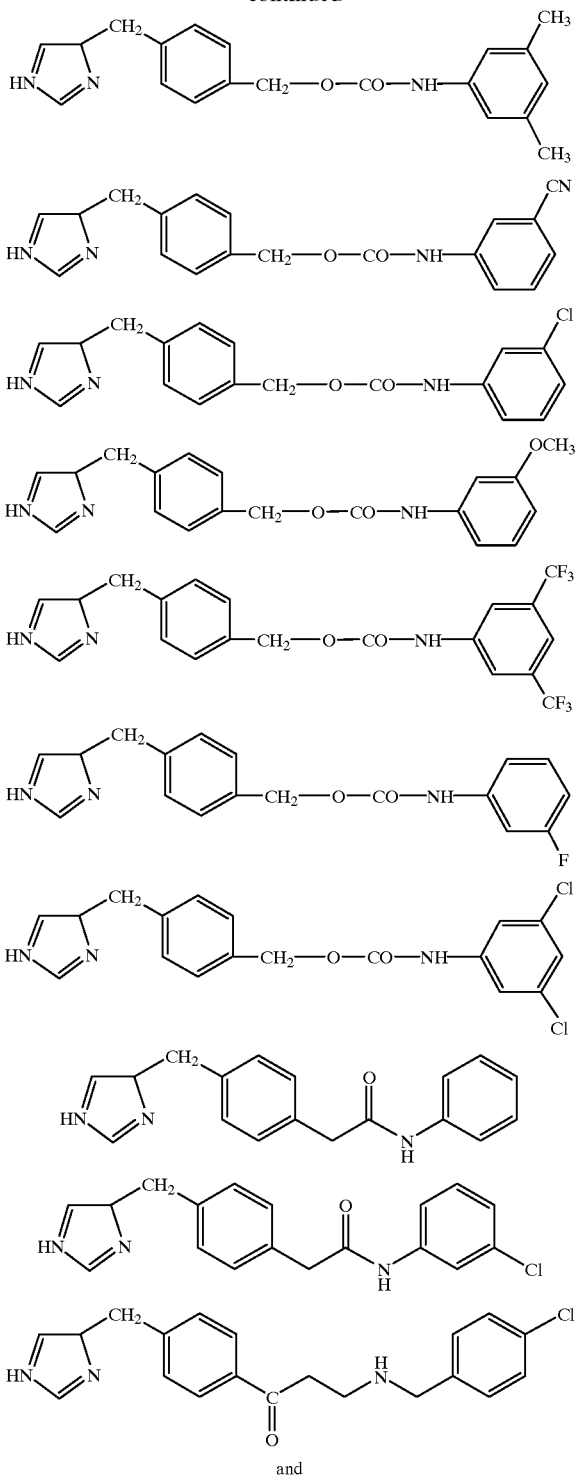

and

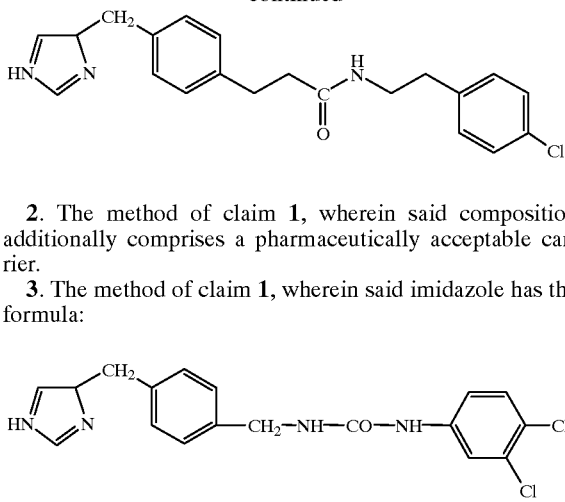

2. The method of claim 1, wherein said composition additionally comprises a pharmaceutically acceptable carrier.

3. The method of claim 1, wherein said imidazole has the formula:

4. The method of claim 1, wherein the amount of imidazole administered to said patient is in the range of about 1 mg/kg to about 5 g/kg of body weight per day.

5. The method of claim 4, wherein the amount of imidazole administered to said patient is in the range of about 1 mg/kg to about 1 g/kg of body weight per day.

6. The method of claim 4, wherein the amount of imidazole administered to said patient is in the range of about 1 mg/kg to about 500 mg/kg of body weight per day.

7. The method of claim 1 wherein said composition is administered orally.

8. The method of claim 1, wherein said composition is administered nasally.

9. The method of claim 1, wherein said composition is administered in solid form.

10. The method of claim 1, wherein said composition is administered in liquid form.

11. The method of claim 2, wherein said pharmaceutically acceptable carrier is selected from the group consisting of lactose, starch, sucrose, cellulose, magnesium stearate, dicalcium phosphate, calcium sulfate, talc, mannitol, ethyl alcohol, and mixtures thereof.

12. The method of claim 2, wherein said pharmaceutically acceptable carrier contains diluent, binder, lubricant, disintegrating agent, coloring agent and mixtures thereof.

13. The method of claim 12, wherein said binder is selected from the group consisting of starch, gelatin, natural sugars, corn sweeteners, acacia, sodium alginate, carboxymethylcellulose, polyethylene glycol, waxes and mixtures thereof.

14. The method of claim 12, wherein said lubricant is selected from the group consisting of boric acid, sodium benzoate, sodium acetate, sodium chloride, and mixtures thereof.

15. The method of claim 12, wherein said disintegrant is selected from the group consisting of starch, methylcellulose, guar gum and mixtures thereof.

* * * * *